United States Patent
Faersnes et al.

(10) Patent No.: US 8,311,603 B2
(45) Date of Patent: Nov. 13, 2012

(54) DEVICE FOR AN ELECTRODE PART FOR A WIRELESS BIOPOTENTIAL MEASUREMENT UNIT

(75) Inventors: Torjus Faersnes, Vegardshei (NO); Rune Fensli, Faervik (NO)

(73) Assignee: Wireless Patient Recording Medical AS (NO)

( * ) Notice: Subject to any disclaimer, the term of this patent is extended or adjusted under 35 U.S.C. 154(b) by 284 days.

(21) Appl. No.: 12/681,876

(22) PCT Filed: Sep. 26, 2008

(86) PCT No.: PCT/NO2008/000343
§ 371 (c)(1),
(2), (4) Date: Jun. 15, 2010

(87) PCT Pub. No.: WO2009/048334
PCT Pub. Date: Apr. 16, 2009

(65) Prior Publication Data
US 2010/0256474 A1 Oct. 7, 2010

(30) Foreign Application Priority Data
Oct. 9, 2007 (NO) .................................. 20075107

(51) Int. Cl.
*A61B 5/0408* (2006.01)
(52) U.S. Cl. ......... 600/372; 600/391; 600/392; 600/393
(58) Field of Classification Search .................. 600/372, 600/391–393
See application file for complete search history.

(56) References Cited

U.S. PATENT DOCUMENTS

| 3,868,947 A | 3/1975 | Holsinger |
| 4,763,660 A | 8/1988 | Kroll et al. |
| 8,050,733 B2 * | 11/2011 | Rytky ........................... 600/388 |
| 2002/0019588 A1 | 2/2002 | Marro et al. |
| 2002/0026112 A1 | 2/2002 | Nissila et al. |
| 2006/0025666 A1 * | 2/2006 | Getsla et al. .................. 600/372 |

FOREIGN PATENT DOCUMENTS
WO 2004/054442 A1 7/2004

OTHER PUBLICATIONS
International Search Report for parent application PCT/NO2008/000343, having a mailing date of Dec. 22, 2008.

* cited by examiner

Primary Examiner — Lee S Cohen
(74) Attorney, Agent, or Firm — Andrus, Sceales, Starke & Sawall, LLP

(57) ABSTRACT

A device for an electrode part for a wireless biopotential measurement unit for attaching to the body, the measurement unit comprising a signal processor and transmitter part, and the electrode part including at least one measuring electrode for measuring a biopotential, the at least one measuring electrode communicating with the signal processor and transmitter part, at least the electrode part being provided with, on its side facing away from the body, a substantially covering screen material which is electrically connected to an earth electrode, the earth electrode being in contact with the body. The measuring electrode is surrounded by and isolated from an electrically conductive material, which is earthed to the signal processor and transmitter part.

8 Claims, 3 Drawing Sheets

DEVICE FOR AN ELECTRODE PART FOR A WIRELESS BIOPOTENTIAL MEASUREMENT UNIT

CROSS-REFERENCE TO RELATED APPLICATIONS

This application is the U.S. national stage application of International Application No. PCT/NO2008/000343, filed Sep. 26, 2008, which International application was published on Apr. 16, 2009, as International Publication No. WO 2009/048334 A1 in the English language, which application is incorporated herein by reference. The International application claims priority of Norwegian Patent Application No. 20075107, filed Oct. 9, 2007, which application is incorporated herein by reference.

BACKGROUND

This invention relates to an electrode part for a wireless biopotential measurement unit. More particularly, it relates to an electrode part for a wireless biopotential measurement unit, called measurement unit below, for attaching to the body of a living organism, the measurement unit including a signal processor and transmitter unit, the electrode part including at least one electrode for measuring a biopotential, the at least one electrode communicating with the signal processor and transmitter unit. On its side facing away from the body, the electrode part is provided with a substantially covering, electrically conductive screen material which is electrically connected to an earth electrode, the earth electrode being in contact with the body.

In what follows, the invention is explained with reference to ECG monitoring, as ECG monitoring adequately illustrates the conditions prevalent during the measuring of a biopotential which is defined as an electrical potential measured between different points on a living organism.

Traditionally, patients, whether human beings or animals, that have a need for periodical or continuous ECG monitoring, have been dependent on being connected to wire-bound monitoring equipment which must, in the main, be monitored continuously by qualified personnel with respect to the values and patterns of the signals, among other things.

It is known to communicate real-time ECG signals by means of a radio link, and the patient thereby has the freedom to carry the measurement equipment and transmitter part with him/her. This means that during the monitoring the patient may move and for example take part in sports activities.

A wireless measurement unit is placed on the patient's body, the measurement unit possibly being a disposable unit. The wireless measurement unit may include an electrode part which is connected to a signal processor and transmitter unit, the electrode part being formed with at least one electrode.

Experience has shown that such movement and rubbing contact between the prior art ECG electrode part and clothing lead to, in part, major interference in the measuring values from said electrode components. Signal filtering may remedy the problem to some extent but may at the same time cause the signal to be distorted or changed in some other unfortunate way.

SUMMARY

The invention has for its object to remedy or reduce at least one of the drawbacks of the prior art.

The object is achieved according to the invention through the features which are specified in the description below and in the claims that follow.

An electrode part in accordance with the invention for a wireless biopotential measurement unit for attaching to the body, the measurement unit comprising a signal processor and transmitter unit, and the electrode part including at least one electrode for measuring a biopotential, the at least one electrode communicating with the signal processor and transmitter unit, is characterized by at least the electrode part being provided with, on its side facing away from the body, a substantially covering, electrically conductive screen material which is electrically connected to an earth electrode, the earth electrode being in contact with the body.

The earth electrode may be constituted by a substantially dot-shaped electrode. Alternatively, the earth electrode may, at least partially, surround at least one measuring electrode.

The screen material over the electrode part serves a double purpose in equalizing differences in potential relative to the skin of the body in the area in which the electrodes are placed, and in the form of an interference-limiter between the electrodes through a low-pass filter formed by the measurement points of the electrode part relative to the screen material.

By connecting the screen plane to the skin of a living organism via a separate electrode, the difference in potential between the skin and screen plane is equalized, so-called "common mode rejection".

Static equalization of differences in potential has as a result that external disturbances or influences are reduced so that the measurement signal has a better signal quality. An ideally conductive plane above the electrode part will mean a convergence plane in which the electrical (E) field viewed along this plane will approximately equal zero ($\bar{E} \approx 0$). This means that electrostatic influence makes to relatively no great extent an electrical field contribution between electrode points located on the underside of the screen material. This is under the condition that the distance d between the conductive screen plane and the electrodes is very small and approximately equal to zero ($d \approx 0$). Besides, a low-pass filtering of the measurement signal is achieved which may reduce unwanted influence within the desired frequency range for the measurement signal, which is assumed to be, for the measuring of ECG signals, between 0.05 Hz and 150 Hz. This is achieved through a capacitive influence between the measuring electrodes and the ideally conductive screen material, the capacitance being given by:

$$C1 = \frac{A}{d} \varepsilon o \cdot \varepsilon r$$

in which $\varepsilon o$ and $\varepsilon r$ are, respectively, the absolute and the relative dielectric constants of the relevant material used in the connection between the ideally conductive plane, the screening material, and an electrode point on the underside of this plane, d being the distance between them and A being the area of the electrode area. Relatively speaking, between two measuring electrodes a and b located on the underside of the screen material there will be a serial connection of two such capacitances, either of them forming the capacitance between the electrode point and the screen material, and such a connection in series of capacitances being connected in parallel with a resistance between the measuring electrodes, the resistance between the measuring electrodes being the resistance in the skin between the measuring electrodes.

The connection in parallel of the resulting capacitance towards the screen plane and the resistance in the skin of the living organism between the electrodes Rh results in a low-pass filtering of the measurement signal, so that the bandwidth B is determined by:

$$B = \frac{1}{2\pi \cdot Rh \cdot 2C1}$$

in which C1 is the capacitance between an electrode and the screen plane and Rb is the resistance in the skin between the electrodes. The overlapping area of the screen plane with the electrodes and the distance between the electrodes is adjusted in relation to the desired bandwidth for the relevant signals, such as ECG signals.

The contact path between the substantially covering screen material and earth electrode may extend through the electrode part or externally relative to it.

With advantage, the electrode part is constituted by a multi-layered flexible material, in which the different metal layers may be provided with, for example, screening, capacitive or inductive components. The intermediate insulating plates have dielectric properties. With respect to electrostatic screening, the operation of the electrode part is based on the establishing of an approximately potential-free area around the measuring electrodes, the measurement signal being constituted essentially by the biopotential of interest, which is desirably to be measured between the different points on the living organism.

When an item of clothing is rubbing against screen material or a material covering the screen material, electrons may become torn away, whereby a build-up of potential may occur. However, this is equalized by means of the electrically conductive connection between the body and the screen material, so that the body and the screening material always have the same potential. It may still happen that a potential is built up between the screen material and the layers located within. To prevent the signal from being attenuated within the measuring range, for example between 0.05 and 150 Hz, it may be advantageous to reduce the capacitance between the measuring electrodes by removing a conductive material from an area near the measuring electrodes, see the particular part of the description. Across the actual electrode the distance to the nearest conductive layer should be at least ⅕₀ of the radius of the electrode.

The capacitance between the different layers must be adjusted so that the impedance in the transmission line from the electrodes is as low as possible for frequencies within the specified measuring range. In addition, the impedance in the actual electrode and the transition between the measuring electrode and the body in the outer layers of the skin must be adjusted to provide good electrical contact.

The contact path from the measuring electrodes to the signal processor and transmitter part is formed symmetrical to avoid electrical interference, so-called "common mode rejection".

These features make the measurement signal remain essentially unaffected even when there is rubbing between clothes and the electrode part.

The measuring electrodes are fixedly spaced in the electrode part and the distance between the measuring electrodes counted along the skin of the body is approximately constant even when the body is moving. This helps to make the measurements relatively stable also when the patient is moving.

The height of the electrode part is relatively small and normally substantially smaller than the width of the electrode part. Normally, the height is smaller than 0.3 times the width and most advantageously smaller than 0.05 times the width.

The height of the electrode part works together with the relatively flexible material to make the electrode part pliable with respect to bending and twisting. Thereby, the electrode part shapes itself to the body when it is adhered to the skin, which limits changes in electrical potential between the body and the electrode part during movement.

The signal processor and transmitter part, which typically includes, in addition to a battery, a signal amplifier and a radio transmitter according to the prior art known per se, may be formed with different filters and also other signal-processing components.

One of the inner conductive layers of the electrode part is typically connected to the battery to provide a reference potential for the signals that are picked up in the measuring electrodes. This earthing layer is independent of the outer earthing/interference-screening layer which is connected to the earth electrode to achieve an approximately potential-free area at the electrode part.

In one embodiment the signal processor and transmitter part may be provided with signal-analysing functions with associated alarm criteria so as to be able to output a signal if the measured signal values fall outside a limit or a signal pattern.

When the measurement unit is adhered to the skin of the body at an appropriate place, bioelectrical measurement signals are transmitted from the measuring electrodes to the signal processor and transmitter part. Any induced electrical signals from rubbing and bending are picked up by the substantially covering, electrically conductive material and are carried to the patient via the earth electrode without disturbing the measurement signals to any extent worth mentioning.

BRIEF DESCRIPTION OF THE DRAWINGS

In what follows is described a non-limiting example of a preferred embodiment which is visualized in the accompanying drawings, in which.

DETAILED DESCRIPTION OF THE DRAWINGS

Figure 1:
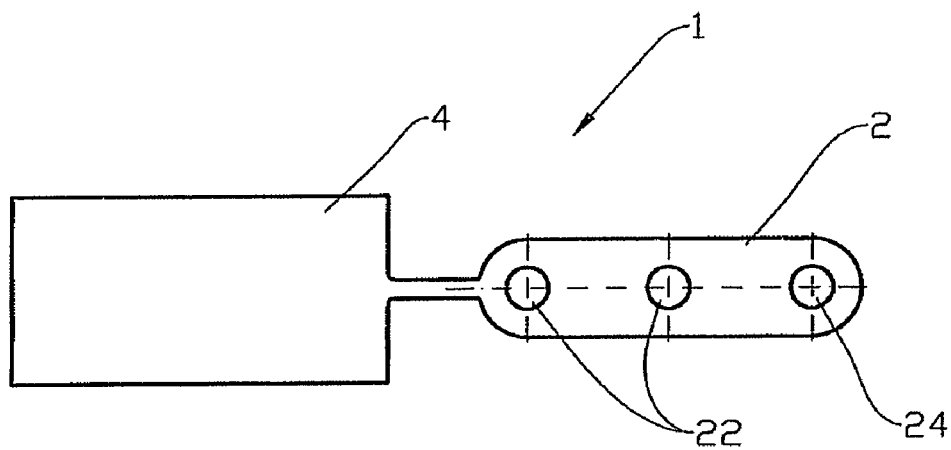
FIG. 1 shows a plan view of a wireless measurement unit for ECG signals, the measurement unit including an electrode part, viewed from the side facing the body.
Figure 2:
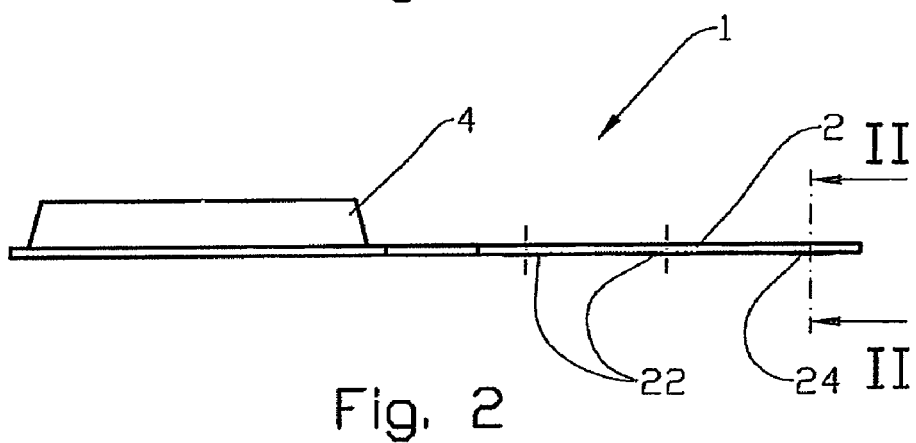
FIG. 2 shows a side view of the measurement unit of FIG. 1.
Figure 3:
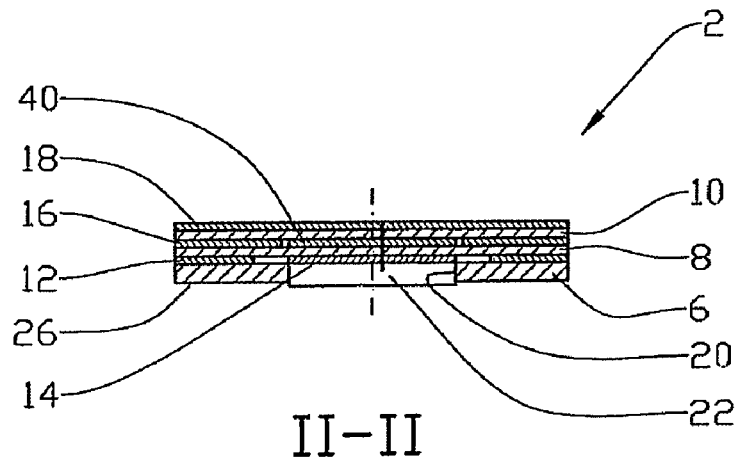
FIG. 3 shows, on a larger scale and schematically, a section II-II of FIG. 2.

In the drawings the reference numeral 1 indicates a measurement unit for ECG signals, the measurement unit 1 comprising an electrode part 2 and a signal processor and transmitter unit 4.

The signal processor and transmitter unit 4 is formed in accordance with the features which are described in the general part of the application and will not be described any further here.

The electrode part 2 includes a number of relatively flexible and thin electrically insulating plates 6, 8 and 10 and several electrically conductive materials 12, 14, 16 and 18, the electrode part 2 being given a relatively elongated, rounded shape.

Figure 4:
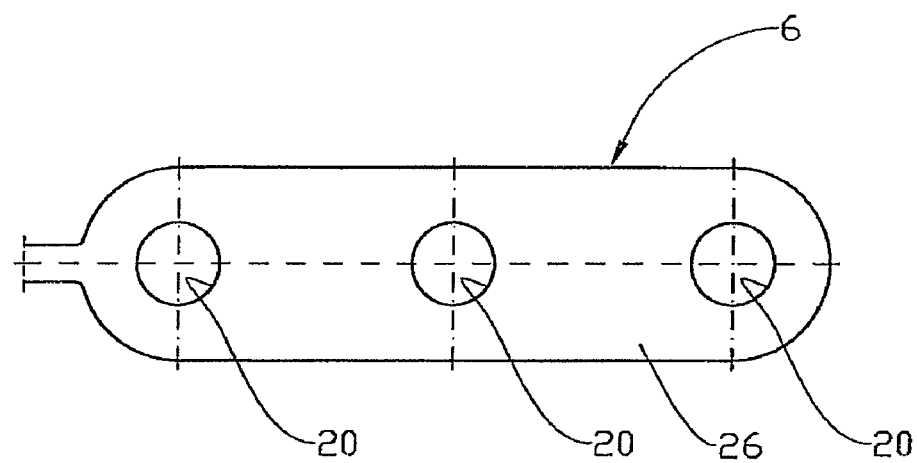
FIG. 4 shows a first electrically insulating plate which is placed, in its position of use, nearest to the patient's body.

A first electrically insulating plate 6 is formed with three through openings 20 complementarily fitting two measuring electrodes 22 and an earth electrode 24, see FIG. 4. The electrodes 22, 24 are constituted by hydrogel electrodes in accordance with the prior art known per se.

The first plate 6 is provided, on one side, with an adhesive 26 of so-called medical quality and is glued, on the opposite side, to a second electrically insulating plate 8.

Figure 5:
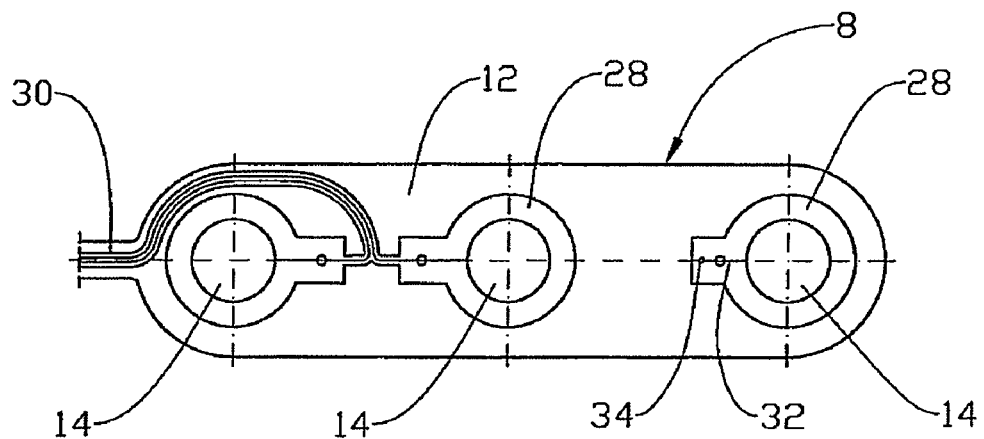
FIG. 5 shows a metal pattern located on the side of a second electrically insulating plate facing the body.

The second plate 8 is formed, on its side facing the first plate 6, with a first metal coating 12 in the form of a copper coating, see FIG. 5.

The first metal coating 12 is formed with through cut-outs 28 and first and second conductor paths 30, 32. In the cut-outs 28 a silver coating 14 has been applied, complementarily matching the openings 20 and arranged to form contact surfaces for the respective electrodes 22, 24.

The first metal coating 12 is earthed in the signal processor and transmitter part 4.

The first conductor paths 30 extend essentially parallel to each other from their respective measuring electrodes 22 to the signal processor and transmitter part 4. The second conductor path 32 extends from the earth electrode 24 to a through opening 34 in the second plate 8.

Figure 6:
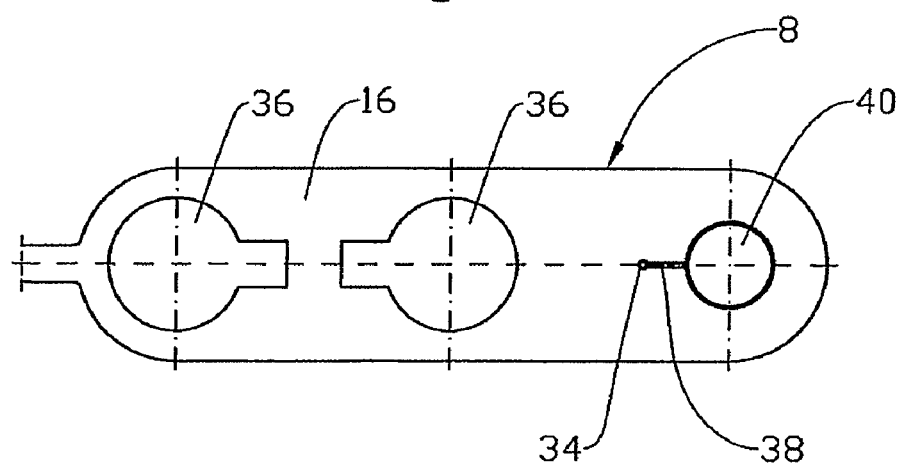
FIG. 6 shows a metal pattern which is located on the opposite side of the second electrically insulating plate.

On its opposite side relative to the first metal coating 12, the second plate 8 is provided with a second metal coating 16 in the form of a copper coating, see FIG. 6. Through cut-outs 36 substantially correspond to the cut-outs 28 of the first metal coating 12. A third conductor path 38 extends from the opening 34, in which it is connected to the second conductor path 32, to a surface 40 partitioned from the rest of the second metal coating 16. The second metal coating 16 forms part of the earth plane of the signal processor and transmitter part 4.

Figure 7:
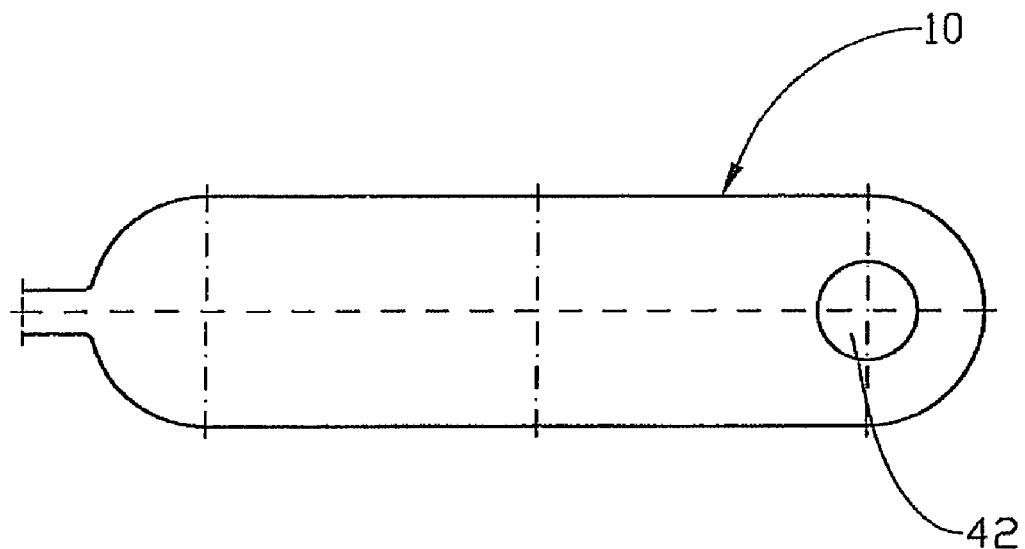
FIG. 7 shows a third electrically insulating plate.
Figure 8:
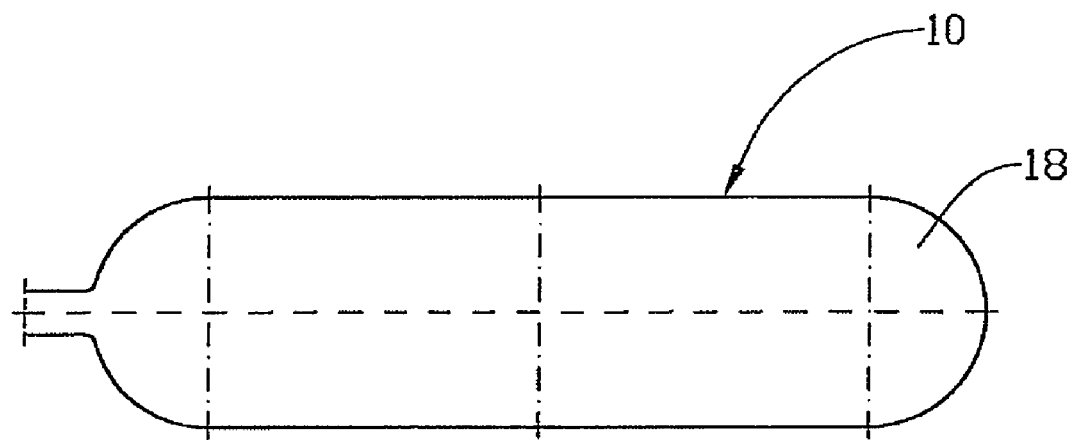
FIG. 8 shows an electrically conductive material located on the side of the third electrically insulating plate facing away from the body.

A third insulating plate 10, see FIG. 7, is glued to the second insulating plate 8 over the second metal coating 16. An electrically conductive screen material 18, see FIG. 8, covers the third insulating plate 10 and is electrically connected to the surface 40 via a conductor 42.

The screen material 18 is thus connected to the earth electrode 24 via its respective silver coating 14, the second conductor path 32, the third conductor path 38 and the conductor 42. The third metal coating thereby forms a screen which is earthed to the skin of a living organism not shown.

One or more of the electrically insulating plates 6, 8 and 10 may be formed of polyamide or polypropylene, for example. The total building height of the electrode part 1 is normally in the order of a millimetre, which causes the electrode part 1 to have little resistance to twisting and bending.

The relatively large cut-outs 28 and 36 in the metal coatings 12 and 16 around the measuring electrodes 22 have the effect of reducing a capacitive coupling between the measuring electrodes 22 and screen material 18 to a desired level, so that within the bandwidth of the measurement signal undesired measurement interference from static discharges is not transmitted.

Before it is put to use, the electrode part 2 includes a protective foil, not shown, which covers the adhesive side of the electrode part 2 and electrodes 22, 24 and is arranged to be removed. Besides, with advantage, the electrode part 2 is covered by a protective material not shown.

After the protective foil not shown has been removed, the measurement unit 1 is adhered to the skin of the living organism, not shown, at an appropriate place. Bioelectrical measurement signals are transferred from the measuring electrodes 22 via the respective silver coating 14 and conductor paths 30 to the signal processor and transmitter part 4.

Any electrical signals induced from rubbing and bending are picked up by the screen material 18 and carried to the living organism via the earth electrode 24 without interfering with the measurement signals to any extent worth mentioning.

The invention claimed is:

1. A measurement unit for measuring a biopotential, the measurement unit comprising an electrode part for attaching, to the body of a living organism body, and a signal processor and transmitter part, the electrode part comprising a first side for attaching to the body and a second, opposite side for facing away from the body, the electrode part further comprising at least one measuring electrode oriented towards the first side of the electrode part for measuring a biopotential, the at least one measuring electrode communicating with the signal processor and transmitter part, and the electrode part being provided with, on the second side, an electric conductive screen material, the screen material being electrically connected to an earth electrode, the earth electrode oriented towards the first side and adapted to be in contact with the body, the electrode part further comprising an electrically conductive material that is earthed to the signal processor and transmitter part, wherein the at least one measuring electrode is surrounded by and electrically isolated from the electrically conductive material.

2. The measurement unit in accordance with claim 1, wherein the earth electrode is substantially spot-shaped.

3. The measurement unit in accordance with claim 1, wherein the earth electrode surrounds, at least partially, the at least one measuring electrode.

4. The measurement unit in accordance with claim 1, wherein a contact path between the screen material and the earth electrode extends through the electrode part.

5. The measurement unit in accordance with claim 1, wherein the electrode part is formed by a multilayered flexible material.

6. The measurement unit in accordance with claim 1, wherein the height of the electrode part is smaller than 0.25 times the width.

7. The measurement unit in accordance with claim 1, wherein the at least one measuring electrode is one of at least two measuring electrodes, wherein the measurement unit is configured such that the distance between the at least two measuring electrodes is approximately constant during movement of the body.

8. The measurement unit in accordance with claim 1, wherein the at least one measuring electrode is one of at least two measuring electrodes, and comprising first contact paths from the at least two measuring electrodes to the signal processor and transmitter part that lay next to each other and are parallel.

\* \* \* \* \*